United States Patent [19]

Finney

[11] Patent Number: 4,532,920
[45] Date of Patent: Aug. 6, 1985

[54] PENILE IMPLANT

[75] Inventor: Roy P. Finney, Tampa, Fla.

[73] Assignee: Medical Engineering Corporation, Racine, Wis.

[21] Appl. No.: 478,449

[22] Filed: Mar. 24, 1983

Related U.S. Application Data

[63] Continuation-in-part of Ser. No. 150,231, May 15, 1980, Pat. No. 4,318,396, and a continuation-in-part of Ser. No. 266,455, May 22, 1981, abandoned, and a continuation-in-part of Ser. No. 328,827, Dec. 9, 1981, Pat. No. 4,411,261.

[51] Int. Cl.³ .............................................. A61F 5/00
[52] U.S. Cl. ..................................................... 128/79
[58] Field of Search .................................. 128/79; 3/1

[56] References Cited

U.S. PATENT DOCUMENTS

| | | | |
|---|---|---|---|
| 3,853,122 | 12/1974 | Strauch et al. | 128/79 |
| 3,954,102 | 5/1976 | Buuck | 128/79 |
| 4,009,711 | 3/1977 | Uson | 128/79 |
| 4,066,073 | 1/1978 | Finney et al. | 128/79 |
| 4,201,202 | 5/1980 | Finney et al. | 128/79 |
| 4,253,201 | 3/1981 | Ross et al. | 3/36 |
| 4,318,396 | 3/1982 | Finney | 128/79 |
| 4,353,360 | 10/1982 | Finney et al. | 128/79 |

FOREIGN PATENT DOCUMENTS

WO80/00302  3/1980  World Intel. Prop. Org. ...... 128/79

Primary Examiner—Dalton L. Truluck
Attorney, Agent, or Firm—Quarles & Brady

[57]  ABSTRACT

A penile prosthesis which is adapted to be surgically implanted in man for the treatment of erectile impotence includes two separate penile implants each comprising an elongated, flexible rod having a short proximal portion of relatively stiff material which is adapted to be implanted into the root end of the corpus cavernosum to support the implant and a longer distal portion which is adapted to be implanted into the corpus cavernosum of the pendulous penis. A flexible, cylindrical sleeve is positioned axially about an intermediate section of the distal portion of the rod and is sealed at its ends to the rod in a fluid tight manner to form a chamber for pressurizing fluid. The implant also includes sealable means by which pressurizing fluid can be added to the chamber to increase the girth of the implant.

5 Claims, 7 Drawing Figures

PENILE IMPLANT

RELATED APPLICATIONS

This application is a continuation-in-part of my earlier applications Ser. No. 150,231 filed May 15, 1980, now U.S. Pat. No. 4,318,396; Ser. No. 266,455 filed May 22, 1981, now abandoned and Ser. No. 328,827 filed Dec. 9, 1981, now U.S. Pat. No. 4,411,261.

FIELD OF THE INVENTION

The present invention relates to a novel penile implant which can be used in the treatment of erectile impotence. More particularly, it relates to an improved rod-type penile implant.

BACKGROUND OF THE INVENTION

There are instances or erectile impotence in which the patient does not respond to more conventional therapy, and the surgical implanting of a penile prosthesis is the only practical means of remedying the impotency.

In the past, several types of implantable penile prostheses have been employed. The first and most common type is a pair of identical rods of suitable stiffness. Each of the rods is surgically implanted into a corpus cavernosum of the penis. The implants disclosed in U.S. Pat. Nos. 3,853,122 and 4,066,073 are representative of this type of penile prosthesis.

Another type of penile prosthesis which is available is the inflatable prosthesis. The most common inflatable prosthesis includes a pair of fairly long inflatable and expandable tubes. Each of the tubes is surgically implanted in a corpus cavernosum of the penis. The two tubes are connected by tubing to a pressure bulb of inflating fluid which is implanted elsewhere in the body. Because of the volume required to pressurize, inflate and expand the inflatable tubes, the pressure bulbs are relatively large. For example, in U.S. Pat. No. 3,954,102, an inflatable prosthesis is disclosed in which the fluid is supplied from a single relatively large reservoir which is implanted in the abdominal cavity. The prosthesis of U.S. Pat. No. 4,009,711 includes two implants each having its own relatively large pressurizing bulb which is surgically implanted in the scrotal sac.

The inflatable type implant has an advantage over the rod-type implant in that its size can be increased to provide a more natural erection. On the other hand, the rod-type implant is more dependable as the inflatable type can develop leaks.

In U.S. Pat. No. 4,201,202 a novel implant is disclosed which is a combination rod-type and inflatable prosthesis. The prosthesis consists of a pair of rod implants, preferably of the type disclosed in U.S. Pat. No. 4,066,073, which have been provided with a flexible sleeve positioned and sealed axially about an intermediate portion of the rod to form a chamber for pressurizing fluid. The implants also each have a pressure bulb of pressurizing fluid connected by tubing to the chamber is that it can be pressurized and a valve to depressurize the chamber. An erection of the penis can be achieved with the patented implant by pressurizing the chambers if a soft rod is used or by manually moving the implants to an erect position if a stiffer hinged rod is used. The implant has an advantage over the conventional rod implant in that it can be pressurized to increase its girth.

SUMMARY OF THE INVENTION

It is the general object of the present invention to disclose an improved rod-type penile implant which can be pressurized to increase its size.

The penile implant of the present invention includes an elongated, flexible rod having a short, proximal portion of relatively stiff material which is adapted to be implanted into the root end of the corpus cavernosum to support the implant and a longer distal portion preferably of a softer and less stiff material which is adapted to be implanted in the corpus cavernosum of the pendulous penis. A flexible, cylindrical sleeve of distensible material is positioned axially about an intermediate section of the distal portion of said rod and the ends of the sleeve are sealed to the rod in a fluid tight manner to form a chamber for receiving pressurizing fluid. The implant also includes sealable means through which pressurizing fluid can be added to the chamber.

The implant of the present invention differs structurally from that of U.S. Pat. No. 4,201,202 in that it has no pressure bulb or connective tubing. As a result, the entire implant can be implanted within the corpus cavernosum of the penis without the need for additional surgery. The implant of the present invention once implanted can be incrementally pressurized over an extended period of time to gradually stretch the tissue of the penis and increase its girth.

In a preferred embodiment of the invention, the tip of the distal portion of the implant is paraboloidal in shape to fit the end of the corpus cavernosum, and it contains a self-sealing valve which permits fluid to be introduced into the chamber with a hollow needle to pressurize the chamber.

DESCRIPTION OF THE PREFERRED EMBODIMENT

Figure 1:
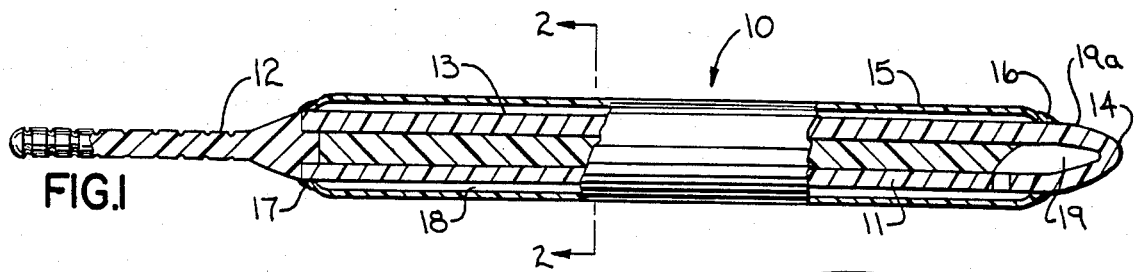
FIG. 1 is a side view, partly in section, of one embodiment the penile implant of the present invention with the chamber in an unpressurized state.

As seen in FIGS. 1-4, the penile implant 10 comprises an elongated rod 11 of a physiologically inert material such as medical application silicone rubber. The rod 11 has a short, proximal portion 12 of relatively stiff material which is to be implanted in the root end of the corpus cavernosum to support and anchor the implant, and a longer distal portion 13 of a softer, more flexible material which is to be implanted into the corpus cavernosum of the pendulous penis. The distal portion 13 has a tip 14 which is paraboloidal to conform in shape to the inner end of the corpus cavernosum of the penis.

Positioned axially about an intermediate section of the distal portion 13 is a sleeve 15 which is sealed at its respective ends 16 and 17 to the rod 11 in a fluidtight manner to form a cylindrical chamber 18 for pressurizing fluid 20. The seals between the ends 16 and 17 of the sleeve 15 and the adjacent areas of the rod 11 are preferably made with a suitable silicone adhesive.

Figure 3:
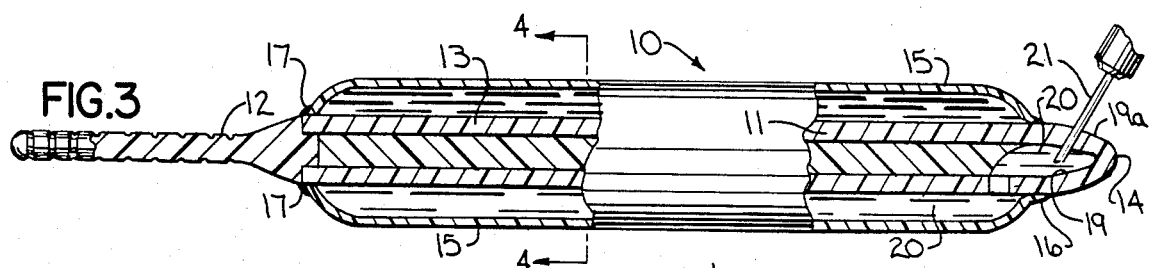
FIG. 3 is a view similar to FIG. 1, showing the chamber being filled and in a pressurized state.

Referring to FIGS. 1 and 3, it can be seen that the tip 14 of the implant 10 is hollow and contains a cavity 19 which communicates with the chamber 18. The wall 19a of the cavity 19 is of a resealable material so that serves as a self sealing valve by which the chamber 18 can be filled with a pressurizing fluid 20 with a hollow needle 21 as seen only in FIG. 4.

Figure 2:
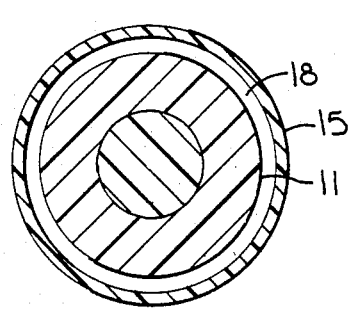
FIG. 2 is a cross sectional view taken along the lines 2—2 of FIG. 1.
Figure 4:
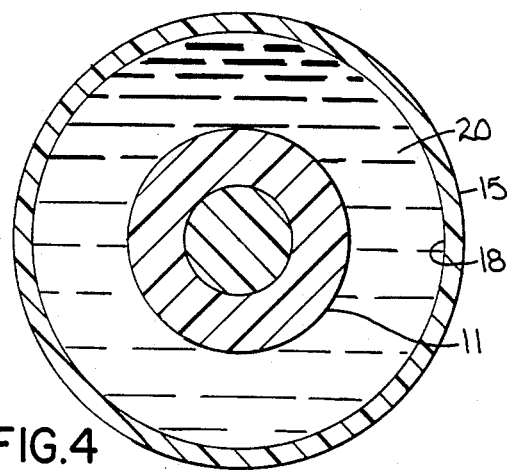
FIG. 4 is a view taken along line 4—4 of FIG. 3.

Referring now to FIGS. 2 and 4, it can be seen that when the chamber 18 is unpressurized the diameter of the implant 10 is substantially less than when the chamber 18 is filled with fluid 20 under pressure. As the chamber 18 is filled the sleeve 15 which is of an elastomeric material expands to increase the girth of the implant 10.

Although in the drawings a single penile implant 10 is shown, as previously described, a complete penile prosthesis will normally include two separate penile implants each of which is surgically implanted in a separate corpus cavernosum of a penis.

When implanted the proximal stem portion 12 of the penile implant 10 is positioned in the root end of the corpus cavernosum to anchor the implant 10, and the paraboloidal tip 14 is positioned in the glans end of the corpus cavernosum. As a result, the implants are at all times positioned correctly in the corpra cavernosum of the penis and the likelihood of displacement is minimized.

To increase the girth of the penis, the chambers 18 of a pair of implanted and properly positioned implants 10 are filled by injecting pressurizing fluid 20 into each of the chambers individually through the hollow needle 21 which is connected to a syringe (not shown). The needle 21 is inserted through the glans of the penis, through the resealable wall 19a of the cavity 19 and into the chamber 18 as seen only in FIG. 4.

Figure 5:
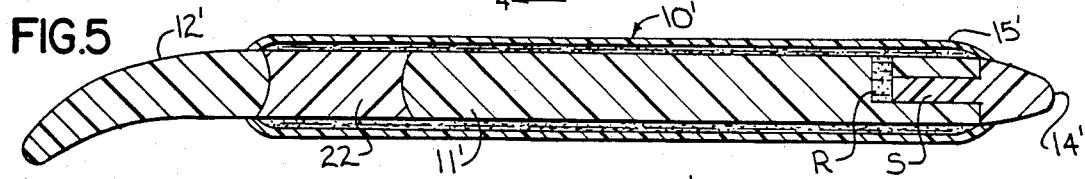
FIG. 5 is side view, in section, of another embodiment of the implant of the present invention.
Figure 6:
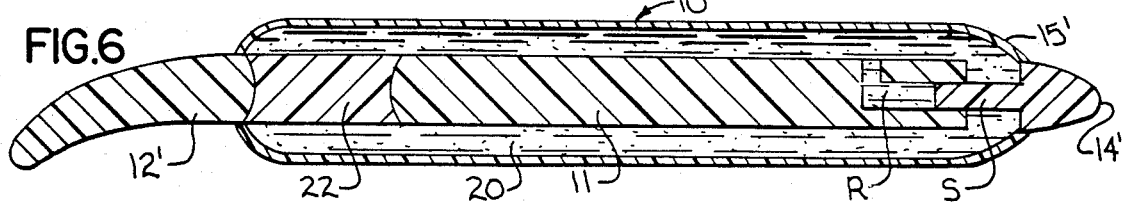
FIG. 6 is view similar to that of FIG. 5 with the chamber pressurized.

In the second embodiment of the invention seen in FIGS. 5 and 6, the rod 11' has the distal and the proximal portions joined by a hinge 22 as is the rod of U.S. Pat. No. 4,066,073. The second embodiment has a unique tip design in which the tip 14' is connected to the sleeve 15'. As seen in FIG. 5, the tip 14' has a stem S which is fully contained in a recess R in the rod 11' when the chamber 18' is unpressurized. When the chamber 18' is pressurized by filling it with fluid under pressure with a needle through sealable means such as a port or an intregal resealable valve (not shown), the pressurizing fluid enters the chamber 18' causing it to increase in diameter and into the recess R causing the tip 14' to move outwardly making the penis in which it is implanted both longer and larger in girth.

The rod of the implant obviously may take other forms than those described. However, the rod should be stiff enough so that even if the chamber 18 is not pressurized the rod will be capable of providing the patient with a usable erection. Therefore, the word "rod" as used in the specification and claims is intended to cover any structure functionally equivalent to those described for purposes of illustration.

In the foregoing description, the proximal portion 12 of the rod 11 has been described as being stiff whereas the distal portion 13 has been described as being relatively flexible. While the term "stiff" has been used to describe the desired physical properties of the material of the rod, a more precise and technical term is flexural modulus, which is the ratio of applied force to resulting deflection. However, most tables of properties do not describe the stiffness properties of rubber or rubber-like material. However, they do list related properties such as hardness.

Hardness is measured by a durometer such as a Shore A durometer which ascertains the depth of penetration of a specific indentor into a specimen under specified conditions. A scale is chosen so that 9 represents a material showing no measurable resistance to indentation and 100 represents a material showing no measurable indentation.

In the preferred embodiment of the invention, the proximal portion 12 of the rod 11 has a Shore hardness of about 70, the distal portion 13 has a Shore hardness of about 20, and the material has sufficient tensile strength for its intended use. Although materials of the described characteristics are preferred, any material which performs satisfactory under conditions of use can be employed.

The sealable means through which pressurizing fluid can be added to the chamber may take several forms. For example, it might be a port which can be plugged or a self-sealing or resealable valve. A suitable material for a resealable valve is disclosed in U.S. Pat. No. 3,919,724.

Figure 7:
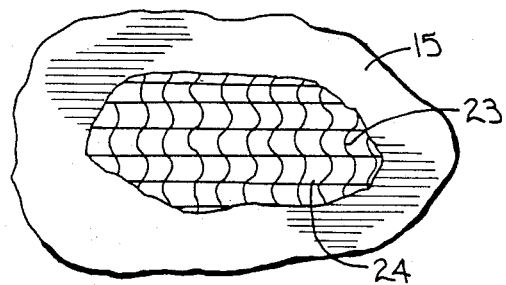
FIG. 7 is an enlarged view of a limited expansion sleeve fabric.

The sleeve 15 preferably is made of an elastomer which will expand when the chamber 18 is pressurized allowing the penis to become larger. However, if desired, the material may be an elastomer coated fabric which will expand to a limited predetermined extent so as to contain the pressure so that the tunica albuginea will not distend. A sample of a coated woven fabric is shown in FIG. 7. As seen in the drawing, the axial threads 23 of the fabric are normally crimped and the longitudinally extending threads 24 are straight. A silicone coated fabric of this design will expand to a limited extent axially and not expand longitudinally.

The preferred method of implantation of implant 10 is through the perineum. After appropriate incision, the corpus cavernosum is dilated distally and proximally to accept the implant. The appropriate anatomical measurements are made to insure that the proximal portion 12 of implant 10 will be positioned at the base of the penis below the pelvic bone. An implant having an appropriately sized distal portion 13 is obtained and the distal portion inserted into the corpus cavernosum of the penis with the tip 14 positioned in the distal end of the corpus cavernosum. The proximal portion 12 of implant 10 may then be cut to the appropriate length.

During the manufacture of implant 10 the length of proximal portion 12 may be deliberately made longer than necessary thereby permitting it to be trimmed to the correct length at the time of surgery. Only one implant of each distal portion length need, therefore, be available since other anatomical length variations may be accommodated by trimming proximal portion 12 and girth variation may be accomodated by pressurizing the chamber 18. This greatly reduces the number of implant sizes which must be produced over that which would be required if no such size alteration were possible. Proximal portion 12 is inserted in the dilated crus after trimming. The incision is then closed. The identical procedure is performed on the other side of the penis to complete the surgical procedure. The distal portions 12 of the two implants may diverge laterally to accommodate the anatomy and provide lateral stability to the penis.

Once the implants have been implanted the chambers 18 are preferably gradually filled with fluid 20 under pressure over an extended period of time to gradually stretch the skin and tissue of the penis to accept the increased girth of the implants.

It will be readily apparent to those skilled in the art that a variety of changes and modifications might be made without departing from the spirit and scope of the invention. Therefore, the scope of the invention is not to be limited except by the claims which follow:

I claim:

1. A rod-type penile implant which can be implanted completely within a corpus cavernosum of a penis and used to incrementally increase the girth of said penis, said implant consisting of:
   (a) an elongated rod-like member of physiologically inert material having a relatively short proximal stem portion adapted to be inserted into the root end of the corpus cavernosum of a penis, and a longer distal portion with a tip adapted to be implanted in the corpus cavernosum of the pendulous penis;
   (b) an integral sleeve axially positioned about an intermediate section of the distal portion of said member and sealed at each end to the member to form an elongated chamber for pressurizing fluid; and
   (c) a self-sealing valve means in said member rod-like and communicating with said chamber whereby pressurizing fluid can be added by means of a body piercing conduit to said chamber from the outside with a catheter so as to incrementally increase the size of said chamber and the girth of a penis in which it is implanted.

2. The implant of claim 1 in which the tip of the member is of resealable material and is the self-sealing valve means.

3. The implant of claim 1 in which the sleeve is of an expandable material.

4. The implant of claim 1 in which the sleeve is comprised of a fabric coated with silicone rubber which fabric expands to a predetermined limited extent to allow the penis to become larger and to contain the pressure so that the tunica albuginea will not distend.

5. The method of incrementally increasing the girth of a penis which comprises implanting in a penis only a pair of implants of claim 1 and later introducing measured amounts of pressurizing fluid into the chambers of said implant with a body piercing conduit through the self-sealing valve means to incrementally expand the chambers and thus stretch the tissue of the penis.

* * * * *